United States Patent
Super et al.

(10) Patent No.: US 10,538,562 B2
(45) Date of Patent: *Jan. 21, 2020

(54) ENGINEERED OPSONIN FOR PATHOGEN DETECTION AND TREATMENT

(71) Applicant: PRESIDENT AND FELLOWS OF HARVARD COLLEGE, Cambridge, MA (US)

(72) Inventors: Michael Super, Lexington, MA (US); Jeffrey Charles Way, Cambridge, MA (US); Donald E. Ingber, Boston, MA (US)

(73) Assignee: PRESIDENT AND FELLOWS OF HARVARD COLLEGE, Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/839,352

(22) Filed: Dec. 12, 2017

(65) Prior Publication Data

US 2018/0094035 A1    Apr. 5, 2018

Related U.S. Application Data

(63) Continuation of application No. 14/831,480, filed on Aug. 20, 2015, now abandoned, which is a continuation of application No. 13/574,191, filed as application No. PCT/US2011/021603 on Jan. 19, 2011, now Pat. No. 9,150,631.

(60) Provisional application No. 61/296,222, filed on Jan. 19, 2010.

(51) Int. Cl.
| C07K 14/77 | (2006.01) |
| C07K 17/00 | (2006.01) |
| C07K 16/44 | (2006.01) |
| G01N 33/569 | (2006.01) |
| C07K 14/47 | (2006.01) |

(52) U.S. Cl.
CPC .......... C07K 14/4726 (2013.01); C07K 16/44 (2013.01); C07K 17/00 (2013.01); G01N 33/56961 (2013.01); *C07K 2317/53* (2013.01); *C07K 2317/66* (2013.01); *C07K 2319/30* (2013.01); *G01N 2333/40* (2013.01)

(58) Field of Classification Search
CPC .... C07K 14/4726; C07K 16/44; C07K 17/00; C07K 2317/53; C07K 2317/66; C07K 2319/30; G01N 2333/40; G01N 33/56961
See application file for complete search history.

(56) References Cited

U.S. PATENT DOCUMENTS

| 4,425,330 A | 1/1984 | Norcross et al. |
| 5,137,810 A | 8/1992 | Sizemore et al. |
| 5,270,199 A | 12/1993 | Ezekowitz |
| 5,273,884 A | 12/1993 | Gale et al. |
| 5,405,832 A | 4/1995 | Potempa |
| 5,474,904 A | 12/1995 | Potempa et al. |
| 5,545,820 A | 8/1996 | Gatehouse et al. |
| 5,585,349 A | 12/1996 | Potempa |
| 5,783,179 A | 7/1998 | Nestor, Jr. et al. |
| 5,874,238 A | 2/1999 | Potempa et al. |
| 5,951,976 A | 9/1999 | Segal |
| 6,057,295 A | 5/2000 | Caretto et al. |
| 6,117,977 A | 9/2000 | Lasky et al. |
| 6,225,046 B1 | 5/2001 | Vesey et al. |
| 6,376,473 B1 | 4/2002 | Audonnet et al. |
| 6,471,968 B1 | 10/2002 | Baker |
| 6,503,761 B1 | 1/2003 | Koenig et al. |
| 6,528,618 B1 | 3/2003 | Fridkin et al. |
| 6,528,624 B1 | 3/2003 | Idusogie et al. |
| 6,562,784 B1 | 5/2003 | Thiel et al. |
| 6,703,219 B1 | 3/2004 | Potempa et al. |
| 6,733,753 B2 | 5/2004 | Boone et al. |
| 6,846,649 B1 | 1/2005 | Thiel et al. |
| 6,900,292 B2 | 5/2005 | Sun et al. |
| 7,182,945 B2 | 2/2007 | Fridkin et al. |
| 7,202,207 B2 | 4/2007 | Thiel et al. |
| 7,211,396 B2 | 5/2007 | Uttenthal |
| 7,226,429 B2 | 6/2007 | Tullis |
| 7,439,224 B2 | 10/2008 | Thiel et al. |
| 7,462,596 B2 | 12/2008 | Larsen et al. |
| 7,566,694 B2 | 7/2009 | Rider |
| 7,629,440 B2 | 12/2009 | Segal et al. |
| 7,695,937 B2 | 4/2010 | Baum |
| 7,763,436 B2 | 7/2010 | Das et al. |

(Continued)

FOREIGN PATENT DOCUMENTS

| EP | 0375736 B1 | 5/1998 |
| EP | 0861667 A3 | 8/2001 |

(Continued)

OTHER PUBLICATIONS

Cooper., "A generic pathogen capucre technology for sepsis diagnosis", retrieved from http://hdl.handle.net/1721.1/83966 (2013).

(Continued)

*Primary Examiner* — Rachael E Bredefeld
*Assistant Examiner* — Erinne R Dabkowski
(74) *Attorney, Agent, or Firm* — Nixon Peabody LLP; David S. Resnick; Nicole D. Kling

(57) ABSTRACT

The present invention provides for engineered molecular opsonins that may be used to bind biological pathogens or identify subclasses or specific pathogen species for use in devices and systems for treatment and diagnosis of patients with infectious diseases, blood-borne infections or sepsis. An aspect of the invention provides for mannose-binding lectin (MBL), which is an abundant natural serum protein that is part of the innate immune system. The ability of this protein lectin to bind to surface molecules on virtually all classes of biopathogens (viruses, bacteria, fungi, protozoans) make engineered forms of MBL extremely useful in diagnosing and treating infectious diseases and sepsis.

5 Claims, 6 Drawing Sheets

Specification includes a Sequence Listing.

(56) References Cited

U.S. PATENT DOCUMENTS

| | | |
|---|---|---|
| 8,013,120 B2 | 9/2011 | Du Clos et al. |
| 8,080,245 B2 | 12/2011 | Visintin et al. |
| 8,084,275 B2 | 12/2011 | Hirai et al. |
| 8,088,596 B2 | 1/2012 | Zeng et al. |
| 8,415,118 B2 | 4/2013 | Huang et al. |
| 8,598,324 B2 | 12/2013 | Rider |
| 9,150,631 B2 | 10/2015 | Super et al. |
| 2003/0162248 A1 | 8/2003 | Wakamiya |
| 2003/0166878 A1 | 9/2003 | Nishiya et al. |
| 2003/0180814 A1 | 9/2003 | Hodges et al. |
| 2004/0018611 A1 | 1/2004 | Ward et al. |
| 2004/0229212 A1 | 11/2004 | Thiel et al. |
| 2005/0014932 A1 | 1/2005 | Imboden et al. |
| 2005/0037949 A1 | 2/2005 | O'Brien et al. |
| 2006/0040362 A1 | 2/2006 | Wakamiya |
| 2006/0104975 A1 | 5/2006 | Geijtenbeek et al. |
| 2006/0177879 A1 | 8/2006 | Mayes et al. |
| 2006/0188963 A1 | 8/2006 | Kongerslev et al. |
| 2006/0251580 A1 | 11/2006 | Keppler et al. |
| 2007/0031819 A1 | 2/2007 | Koschwanez et al. |
| 2007/0049532 A1 | 3/2007 | Feige et al. |
| 2007/0072247 A1 | 3/2007 | Wong et al. |
| 2007/0122850 A1 | 5/2007 | Teng |
| 2007/0184463 A1 | 8/2007 | Molho et al. |
| 2007/0224640 A1 | 9/2007 | Caldwell et al. |
| 2007/0231833 A1 | 10/2007 | Arcidiacono et al. |
| 2007/0269818 A1 | 11/2007 | Savage |
| 2008/0014576 A1 | 1/2008 | Jovanovich et al. |
| 2008/0056949 A1 | 3/2008 | Lee et al. |
| 2008/0108120 A1 | 5/2008 | Cho et al. |
| 2008/0156736 A1 | 7/2008 | Hirai et al. |
| 2008/0182793 A1 | 7/2008 | Baum |
| 2008/0193965 A1 | 8/2008 | Zeng et al. |
| 2008/0260738 A1 | 10/2008 | Moore |
| 2008/0300188 A1 | 12/2008 | Yang et al. |
| 2009/0078614 A1 | 3/2009 | Varghese et al. |
| 2009/0175797 A1 | 7/2009 | Warren et al. |
| 2009/0181041 A1 | 7/2009 | Holgersson et al. |
| 2009/0220932 A1 | 9/2009 | Ingber et al. |
| 2009/0252729 A1 | 10/2009 | Farrington et al. |
| 2009/0269843 A1 | 10/2009 | Blume et al. |
| 2009/0297516 A1 | 12/2009 | Mayo et al. |
| 2010/0044232 A1 | 2/2010 | Lin et al. |
| 2010/0055675 A1 | 3/2010 | Kumamoto |
| 2010/0266558 A1 | 10/2010 | Zipori |
| 2010/0323342 A1 | 12/2010 | Gomez et al. |
| 2010/0323429 A1 | 12/2010 | Hu et al. |
| 2010/0331240 A1 | 12/2010 | Michelow et al. |
| 2011/0027267 A1 | 2/2011 | Kyneb et al. |
| 2011/0053145 A1 | 3/2011 | Takakura et al. |
| 2011/0053250 A1 | 3/2011 | Takakura et al. |
| 2011/0065095 A1 | 3/2011 | Kida |
| 2011/0159000 A1 | 6/2011 | Silverman |
| 2011/0183398 A1 | 7/2011 | Dasaratha et al. |
| 2011/0281792 A1 | 11/2011 | Zion et al. |
| 2012/0100140 A1 | 4/2012 | Reyes et al. |
| 2012/0164628 A1 | 6/2012 | Duffin et al. |
| 2013/0035283 A1 | 2/2013 | Super |
| 2013/0072445 A9 | 3/2013 | Du Clos et al. |

FOREIGN PATENT DOCUMENTS

| | | |
|---|---|---|
| EP | 0915970 B1 | 9/2004 |
| EP | 1862541 A1 | 12/2007 |
| EP | 1812459 B1 | 3/2011 |
| JP | S54-18198 A | 2/1979 |
| JP | 2008515389 A | 5/2008 |
| JP | 2010122205 A | 6/2010 |
| JP | 2010268800 A | 12/2010 |
| WO | 2001/003737 A1 | 1/2001 |
| WO | 02/32292 A2 | 4/2002 |
| WO | 03/014150 A2 | 2/2003 |
| WO | 03/054164 A2 | 7/2003 |
| WO | 2004/018698 A2 | 3/2004 |
| WO | 2005/092925 A2 | 10/2005 |
| WO | 2006/018428 A2 | 2/2006 |
| WO | 2006/044650 A2 | 4/2006 |
| WO | 2007/001332 A2 | 1/2007 |
| WO | 2007/044642 A2 | 4/2007 |
| WO | 2007/111496 A1 | 10/2007 |
| WO | 2008/130618 A1 | 10/2008 |
| WO | 2009/040048 A2 | 4/2009 |
| WO | 2009/062195 A2 | 5/2009 |
| WO | 2009/126346 A2 | 10/2009 |
| WO | 2009119722 A1 | 10/2009 |
| WO | 2000006603 A1 | 12/2010 |
| WO | 2011/084749 A1 | 7/2011 |
| WO | 2011/090954 A2 | 7/2011 |
| WO | 2011/091037 A2 | 7/2011 |
| WO | 2012/100099 A2 | 7/2012 |
| WO | 2012/135834 A2 | 10/2012 |
| WO | 2013/012924 A2 | 1/2013 |

OTHER PUBLICATIONS

Ilyas et al., "High glucose disrupts oligosaccharide recognition function via competitive inhibition: a potential mechanism for immune dysregulation in diabetes mellitus", Immunobiology 216(1-2) 126-131 (2011).

Kjaer et al., "M-ficolin binds selectively to the capsular polysaccharides of Streptococcus pneumoniae serotypes 19B and 19C and of a Streptococcus mitis strain", Infect Immun 81(2) 452-459 (2013).

Zettner et al., "Principles of competitive binding assays (saturation analyses). II. Sequential saturation", Clin Chem 20(1) 5-14 (1974).

Zettner et al., "Principles of competitive binding assays (saturation analysis). 1. Equilibrium techniques", Clin Chem 19(7) 699-705 (1973).

Arakawa et al., "Elution of antibodies from a Protein-A column by aqueous arginine solutions", Protein Expression and Purification 36:244-248 (2004).

Armour et al., "Recombinant human IgG molecules lacking Fcγ receptor I binding and monocyte triggering activities", European Journal of Immunology 29:2613-2624 (1999).

Ashkenazi et al., "Immunoadhesins as research tools and therapeutic agents", Current Opinion in Immunology 9:195-200 (1997).

Azevedo et al., "Horseradish peroxidase: a valuable tool in biotechnology," Biotechnology Annual Review 9:199-247 (2003).

Bangs Laboratories, Inc., "Protein Coated Microspheres", Tech. Note #51 (1997). (4 pages).

Bayston et al., "Bacterial endotoxin and current concepts in the diagnosis and treatment of endotoxaemia", Journal of Medical Microbiology 31:73-83 (1990).

Bossola et al., "Circulating Bacterial-Derived DNA Fragments and Markers of Inflammation in Chronic Hemodialysis Patients", Clinical Journal of the American Society of Nephrology 4:379-385 (2009).

Brooks et al., "Expression and secretion of ficolin β by porcine neutrophils", Biochimica et Biophysica Acta 1624:36-45 (2003).

Brouwer et al., "Mannose-Binding Lectin (MBL) Facilitates Opsonophagocytosis of Yeasts but Not of Bacteria despite MBL Binding", The Journal of Immunology 180:4124-4132 (2008).

Chamow et al., "Immunoadhesins: principles and applications", Trends Biotechnology 14:52-60 (1996).

Chang et al., "Crystallization and Preliminary X-ray Analysis of a Trimeric Form of Human Mannose Binding Protein", Journal of Molecular Biology 241:125-127 (1994).

Chen et al., "Fabrication of an Oriented Fc-Fused Lectin Microarray through Boronate Formation", Angewandte Chemie International Edition 47:8627-8630 (2008).

Foster, "Immune Evasion by *Staphylococci*", Nature 3:948-958 (2005).

Fox et al., "Single amino acid substitutions on the surface of *Escherichia coli* maltose-binding protein can have a profound impact on the solubility of fusion proteins", Protein Science 10:622-630 (2001).

(56) References Cited

OTHER PUBLICATIONS

Frakking et al., "Safety and phamacokinetics of plasma-derived mannose-binding lectin (MBL) substitution in children with chemotherapy-induced neutropaenia", European Journal of Cancer 45:505-512 (2009).
Garred et al., "Mannose-binding lectin and its genetic variants", Genes and Immunity 7:85-94 (2006).
Gouin et al., "Multimeric Lactoside "Click Clusters" as Tools to Investigate the Effect of Linker Length in Specific Interactions with Peanut Lectin, Galectin-1, and -3", ChemBioChem 11:1430-1442 (2010).
Grogl et al., "Leishmania braziliensis: Protein, Carbohydrate, and Antigen Differences between Log Phase and Stationary Phase Promastigotes in Vitro", Experimental Parasitology 63:352-359 (1987).
Hinton et al., "Engineered Human IgG Antibodies with Longer Serum Half-lives in Primates", The Journal of Biological Chemistry 279(8):6213-6216 (2004).
Holmskov et al., "Affinity and kinetic analysis of the bovine plasma C-type lectin collectin-43 (CL-43) interacting with mannan", FEBS Letters 393:314-316 (1996).
Huang et al., "Porcine DC-SIGN: Molecular cloning, gene structure, tissue distribution and binding characteristics", Developmental and Comparative Immunology 33:464-480 (2009).
Hwang et al., "The Pepper Mannose-Binding Lectin Gene CaMBL1 Is Required to Regulate Cell Death and Defense Responses to Microbial Pathogens", Plant Physiology 155:447-463 (2011).
Idusogie et al., "Engineered Antibodies with Increased Activity to Recruit Complement", The Journal of Immunology 166:2571-2575 (2001).
INVIVO GEN Insight, "IgG-Fc Engineering for Therapeutic Use", (2006). (4 pages).
Jack et al., "Mannose-binding lectin: targeting the microbial world for complement attack and opsonophagocytosis", Immunological Reviews 180:86-99 (2001).
Jarva et al., "*Streptococcus pneumoniae* Evades Complement Attack and Opsonophagocytosis by Expressing the pspC Locus-Encoded Hic Protein That Binds to Short Consensus Repeats 8-11 of Factor H", The Journal of Immunology 168:1886-1894 (2002).
Kang et al., "The human macrophage mannose receptor directs *Mycobacterium tuberculosis* lipoarabinomanan-mediated phagosome biogenesis", The Journal of Experimental Medicine 202(7):987-999 (2005).
Keen et al., "Interrelationship Between pH and Surface Growth of Nitrobacter", Soil Biology and Biochemistry 19(6):665-672 (1987).
Kehres, "A kinetic model for binding protein-mediated arabinose transport", Protein Science 1:1661-1665 (1992).
Krarup et al., "Simultaneous Activation of Complement and Coagulation by MBL-Associated Serine Protease 2", PLoS One 2(7):e623 (2007). (8 pages).
Linehan et al., "Endogenous ligands of carbohydrate recognition domains of the mannose receptor in murine macrophages, endothelial cells and secretory cells; potential relevance to inflammation and immunity", European Journal of Immunology 31:1857-1866 (2001).
Lo et al., "High level expression and secretion of Fc-X fusion proteins in mammalian cells", Protein Engineering 11 (6):495-500 (1998).
Loosdrecht et al., "Influence of Interfaces on Microbial Activity", Microbiological Reviews 54(1):75-87 (1990).
Matsushita et al., "Activation of the Classical Complement Pathway by Mannose-binding Protein in Association with a Novel C1s-like Serine Protease", Journal of Experimental Medicine 176(6):1497-1502 (1992).
Michelow et al., "A Novel L-ficolin/Mannose-binding Lectin Chimeric Molecule with Enhanced Activity against Ebola Virus", The Journal of Biological Chemistry 285(32):24729-24739 (2010).
Nadesalingam et al., "Mannose-Binding Lectin Recognizes Peptidoglycan via the N-acetyl Glucosamine Moiety, and Inhibits Ligand-Induced Proinflammatory Effect and Promotes Chemokine Production by Macrophages", The Journal of Immunology 175:1785-1794 (2005).
Nakamura et al., "Characterization of the interaction between serum mannan-binding protein and nucleic acid ligands", Journal of Leukocyte Biology 86:737-748 (2009).
Neth et al., "Mannose-Binding Lectin Binds to a Range of Clinically Relevant Microorganisms and Promotes Complement Deposition", Infection and Immunity 68(2):688-693 (2000).
Neth et al., "Ehancement of Complement Activation and Opsonophagocytosis by Complexes of Mannose-Binding Lectin with Mannose-Binding Lectin-Associated Serine Protease After Binding to *Staphylococcus aureus*", The Journal of Immunology 169:4430-4436 (2002).
Nisnevitch et al., "The solid phase in affinity chromatography: strategies for antibody attachment", Journal of Biochemical and Biophysical Methods 49:467-480 (2001).
Ogden et al., "C1q and Mannose Binding Lectin Engagement of Cell Surface Calreticulin and CD91 Initiates Macropinocytosis and Uptake of Apoptotic Cells", The Journal of Experimental Medicine 194(6):781-795 (2001).
Perham, "Domains, Motifs, and Linkers in 2-Oxo Acid Dehydrogenase Multienzyme Complexes: A Paradigm in the Design of a Multifunction Protein", Biochemistry 30(35):8501-8512 (1991).
Product Datasheet, "Human Mannan Binding Lectin peptide (237-248) (Carboxyterminal end) ab45655".
Rutishauser et al., "Amino Acid Sequence of the Fc Region of a Human γG Immunoglobulin", Biochemistry 61:1414-1421 (1968).
Safarik et al., "The application of magnetic separations in applied microbiology", Journal of Applied Bacteriology 78:575-585 (1995).
Schmidt, "Fusion proteins as biopharmaceuticals—Applications and challenges", Current Opinion in Drug Discovery & Development 12(2):284-295 (2009).
Shields et al., "High Resolution Mapping of the Binding Site on Human IgG1 for FcγRI, FcγRII, FcγRIII, and FcRn and Design of IgG1 Variants with Improved Binding to the FcγR", The Journal of Biological Chemistry 276 (9):6591-6604 (2001).
Sibille et al., "Comparison of serological tests for the diagnosis of feline immunodeficiency virus infection of cats", Veterinary Microbiology 45:259-267 (1995).
Sprong et al., "Mannose-Binding Lectin Is a Critical Factor in Systemic Complement Activation during Meningococcal Septic Shock", Clinical Infectious Diseases 49:1380-1386 (2009).
Steurer et al., "Ex Vivo Coating of Islet Cell Allografts with Murine CTLA4/Fc Promotes Graft Tolerance", The Journal of Immunology 155:1165-1174 (1995).
Stuart et al., "Mannose-Binding Lectin-Deficient Mice Display Defective Apoptotic Cell Clearance but No Autoimmune Phenotype", The Journal of Immunology 174:3220-3226 (2005).
Takahashi et al., "Mannose-binding lectin and its associated proteases (MASPs) mediate coagulation and its deficiency is a risk factor in developing complications from infection, including disseminated intravascular coagulation", Immunobiology 216(1-2):96-102 (2011).
Terai et al., "Relationship between gene polymorphisms of mannose-binding lectin (MBL) and two molecular forms of MBL", European Journal of Immunology 33:2755-2763 (2003).
Thiel et al., "A second serine protease associated with mannan-binding lectin that activates complement", Nature 386:506-510 (1997).
Vaccaro et al., "Engineering the Fc region of immunoglobulin G to modulate in vivo antibody levels", Nature Biotechnology 23(10):1283-1288 (2005).
Ward et al., "Characterization of Humanized Antibodies Secreted by *Aspergillus niger*", Applied and Environmental Microbiology 70(5):2567-2576 (2004).
Warwick et al., "Use of Quantitative 16S Ribosomal DNA Detection for Diagnosis of Central Vascular Catheter-Associated Bacterial Infection", Journal of Clinical Microbiology 42(4):1402-1408 (2004).
Witus et al., "Identification of Highly Reactive Sequences for PLP-Mediated Bioconjugation Using a Combinatorial Peptide Library", Journal of the American Chemical Society 132:16812-16817 (2010).

(56) References Cited

OTHER PUBLICATIONS

Wong et al., "Bioinspired self-repairing slippery surfaces with pressure-stable omniphobicity", Nature 477:443-447 (2011).
Wriggers et al., "Control of Protein Functional Dynamics by Peptide Linkers", Biopolymers (Peptide Science) 80:736-746 (2005).
Xia et al., "Combined microfluidic-micromagnetic separation of living cells in continuous flow", Biomed Microdevices 8:299-308 (2006).
Ye et al., "Surface display of a glucose binding protein", Journal of Molecular Catalysis B: Enzymatic 28:201-206 (2004).
Yung et al., "Micromagnetic-microfluidic blood cleansing device", Lab on a Chip 9:1171-1177 (2009).
Agrawal et al., "C-reactive protein mutant that does not bind to phosphocholine and pneumococcal C-polysaccharide", J. Immunol. 169(6):3217-3222 (2002).
Barnum et al., "Comparative Studies on the Binding Specificities of C-Reactive Protein (CRP) and HOPC 8", Annals of the New York Academy of Sciences 389:431-434 (1982).
Casey et al., "The acute-phase reactant C-Reactive protein binds to phosphorylcholine-expressing Neisseria meningitidis and increased uptake by human phagocytes", Infection and Immunity 76(3): 12998-1304 (2008).
Culley et al., "C-reactive protein binds to phosphorylated carbohydrates", Glycobiology 10(1):59-65 (2000).
Dumont et al., "Monomeric Fc Fusions: Impact on Pharmacokinetic and Biological Activity of Protein Therapeutics", Biodrugs 20(3):151-160 (2006).
Huang et al., "Integrated microfluidic system for rapid screening of CRP aptamers utilizing systematic evolution of ligands by exponential enrichment (SELEX)", Biosensors and Bioelectronics 25:1761-1766 (2010).
Lee et al., "Carbohydrate-binding properties of human neo-CRP and its relationship to phosphorylcholine-binding site", Glycobiology 13(1):11-21 (2003).
Mold et al., "Binding of Human C-Reactive Protein to Bacteria", Infection and Immunity 38(1):392-395 (1982).
Presanis et al., "Biochemistry and genetics of mannan-binding lectin (MBL)", Biochemical Society Transactions 31 (4):748-752 (2003).
Shoulders et al., "Collagen structure and stability." Annual Review of Biochemistry 78(1):929-958 (2009).
Szalai, "The biological functions of C-reactive protein", Vascular Pharmacology 39:105-107 (2002).
Zhavnerko et al., "Oriented Immobilization of C-Reactive Protein on Solid Surface for Biosensor Applications", Frontiers of Multifunctional Integrated Nanosystems 95-108 (2004).
Choma et al. "Design of a Heme-Binding Four-Helix Bundle" 116:856-865 (1994).
Mantuano et al., "The hemopexin domain of matrix metalloproteinase-9 activates cell signaling and promotes migration of schwann cells by binding to low-density lipoprotein receptor-related protein.", The Journal of Neuroscience 28(45):11571-11582 (2008).
Castle et al., "The binding of 125I-labeled concanavalin A to the cell surface of rabbit peritoneal polymorphonuclear leucocytes." Biochemical Medicine 28(1):1-15 (1982).
Feng et al., "Identification of carbohydrates on the surface membrane of pathogenic and nonpathogenic piscine haemoflagellates, Cryptobia salmositica, C. bullocki and C. catostomi (Kinetoplastida)." Diseases of Aquatic Organisms 32(3):201-209 (1998).
Rouhandeh et al., "Surface membrane redistribution and stabilization of concanavalin A-specific receptors following Yaba tumor poxvirus infection." Biochimica et Biophysica Acta (BBA)-Biomembranes 600(2):301-312 (1980).

ENGINEERED OPSONIN FOR PATHOGEN DETECTION AND TREATMENT

CROSS REFERENCE TO RELATED APPLICATIONS

This application is a Continuation of U.S. application Ser. No. 14/831,480, filed Aug. 20, 2015, which is a Continuation of U.S. application Ser. No. 13/574,191, filed Oct. 23, 2012, now U.S. Pat. No. 9,150,631, which is a 35 U.S.C. § 371 National Phase Entry Application of International Application No. PCT/US2011/021603, filed Jan. 19, 2011, which designates the U.S., and which claims the benefit of U.S. Provisional Application No. 61/296,222 filed Jan. 19, 2010, the contents of each of which are incorporated fully herein by reference in their entirety.

SEQUENCE LISTING

The instant application contains a Sequence Listing which has been submitted in ASCII format via EFS-Web and is hereby incorporated by reference in its entirety. Said ASCII copy, created on Aug. 20, 2015, is named 20150820_Sequence_Listing_002806-078071-C.txt and is 7,084 bytes in size.

FIELD OF THE INVENTION

The present invention relates to molecular immunology, microbial pathogens, and systems for detecting and/or removing pathogens in fluids, including bodily fluids such as blood. More specifically, for example, the present invention provides for an engineered molecular opsonin that may be used to bind biological pathogens or identify subclasses or specific pathogen species for use in devices and systems for treatment and diagnosis of patients with infectious diseases, blood-borne infections, or sepsis.

BACKGROUND

In the U.S., sepsis is the second-leading cause of death in non-coronary ICU patients, and the tenth-most-common cause of death overall. Sepsis is a serious medical condition that is characterized by a whole-body inflammatory state (called a systemic inflammatory response syndrome) and the presence of a known or suspected infection. Sepsis typically occurs during bacteremia, viremia or fungemia, and may result from infections that are caused by pathogens, such as *Staphylococcus aureus*, that are not typical bloodborne pathogens. Bloodborne pathogens are microorganisms that cause disease when transferred from an infected person to another person through blood or other potentially infected body fluids. The most common diseases include Hepatitis B, Human Immunodeficiency Virus, malaria, Hepatitis C, and syphilis.

Unfortunately, systemic inflammatory response syndrome may become life threatening before an infective agent has been identified by blood culture. This immunological response causes widespread activation of acute-phase proteins, affecting the complement system and the coagulation pathways, which then cause damage to both vasculature and organs. Various neuroendocrine counter-regulatory systems are also activated, often compounding the problem. Even with immediate and aggressive treatment, this can progress to multiple organ dysfunction syndrome and eventually death. Hence, there remains a need for improved techniques for diagnosis and treatment of patients with infectious diseases, blood-borne infections, sepsis, or systemic inflammatory response syndrome.

SUMMARY

The present invention provides for an engineered molecular opsonin that may be used to bind biological pathogens or identify subclasses or specific pathogen species for use in devices and systems for treatment and diagnosis of patients with infectious diseases, blood-borne infections or sepsis; or in the identification of water- or food-borne pathogens. An aspect of the invention provides for mannose-binding lectin (MBL), which is an abundant natural serum protein that is part of the innate immune system. The ability of this protein lectin to bind to surface molecules on virtually all classes of biopathogens (viruses, bacteria, fungi, protozoans) make engineered forms of MBL extremely useful in diagnosing and treating infectious diseases and sepsis.

An embodiment of the present invention provides for a recombinant opsonin comprising a carbohydrate recognition domain of an opsonin, a substrate binding domain, and a flexible peptide domain that links the recognition domain to the solid surface binding domain. In aspects of the invention, the carbohydrate recognition domain is a lectin or fragment of a lectin. Alternatively, the carbohydrate recognition domain is a collectin or ficollin, or a portion or fragment of these. In a particular aspect, the carbohydrate recognition domain (CRD) comprises the portion of MBL starting at the residue proline 81 at the N-terminal end of the lectin portion of the engineered opsonin. In another particular aspect, the carbohydrate recognition domain comprises the portion of MBL starting at the residue glycine 111 at the N-terminal end of the lectin portion for the engineered opsonin.

In a particular aspect of the invention, the substrate binding domain of the recombinant opsonin comprises one or more cysteine residues that allow chemical cross-linking to a solid substrate. The solid substrate may comprise a magnetic microbead (which may be coated with protein A), a microporous membrane, a hollow-fiber reactor, or any other blood filtration membrane or flow device. In other aspects, the substrate can be the surface of cells, such as immune cells (e.g., macrophages), the surfaces of cells that line the tissues or organs of the immune system (e.g., lymph nodes or spleen), or the surface of the extracellular matrix of tissues or organs of the immune system.

In another aspect of the invention, the flexible peptide domain may comprise at least one Glycine+Serine segment and/or at least one Proline+Alanine+Serine segment. In another aspect of the present invention, the flexible linker is a Fc portion of immunoglobulin, such as Fcγ. Fusion of human IgG1 Fc to the neck and CRD regions of MBL improves the expression and purification and coupling to a substrate in an active form.

An embodiment of the invention provides for a method of collecting an opsonin-binding microorganism from a fluid comprising contacting the fluid with a recombinant opsonin conjugated to a solid surface; wherein the recombinant opsonin consists of a carbohydrate recognition domain of an opsonin, a solid substrate binding domain, and a flexible peptide domain that links the recognition domain to the solid surface binding domain; allowing the opsonin-binding microorganism to bind to said recombinant opsonin-solid surface conjugate; and separating said fluid from said microorganism-bound recombinant opsonin-solid surface conjugate. The fluid may be a biological fluid, such as blood, obtained from a subject. The fluid may then be returned to the subject.

Another embodiment of the invention provide a method of treating a blood infection in a subject comprising administering a recombinant opsonin to the blood of the subject, wherein the recombinant opsonin consists of a carbohydrate recognition domain of an opsonin, a substrate binding domain, and a flexible peptide domain that links the recognition domain to the substrate binding domain, wherein the carbohydrate recognition domain binds an opsonin-binding microorganism, and wherein the substrate binding domain binds with a cell, tissue or organ of the immune system; allowing the recombinant opsonin to bind to the opsonin-binding microorganism; and allowing the microorganism-bound recombinant opsonin to bind with a cell, tissue or organ of the immune system wherein the microorganism is killed. The subject may be an animal or a human.

BRIEF DESCRIPTION OF THE DRAWINGS

FIG. 8A is a western blot of a reduced gel loaded with unpurified supernatant of 293 cells transfected with pFUSEFc MBL.81 (and pFUSE Fc) probed with anti-hFc.

FIG. 8B shows Protein A-purified FcMBL.81.

DETAILED DESCRIPTION

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

In the broadest sense, opsonins are proteins that bind to the surface of a particle. In nature, opsonins act as binding enhancers for the process of phagocytosis, for example, by coating the negatively-charged molecules on a target pathogen's membrane. The present invention provides for an engineered molecular opsonin, such as mannose-binding lectin (MBL), that may be used to bind biological pathogens or identify subclasses or specific pathogen species for use in devices and systems for treatment and diagnosis of patients with infectious diseases, blood-borne infections or sepsis. Treatment may be carried out in vivo or ex vivo.

Figure 1:
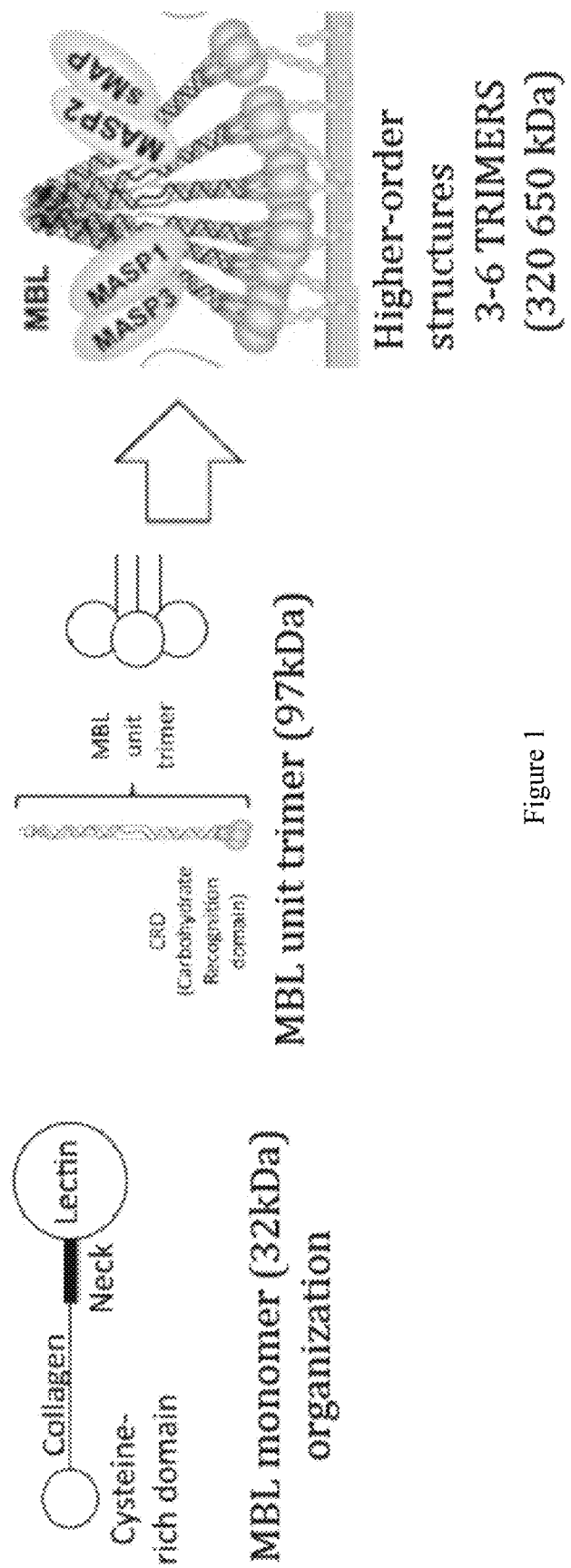
FIG. 1 shows a diagram of mannose-binding lectin (MBL) engineered into sets of trimers (polymers) in an embodiment of the present invention.

MBL is a serum lectin opsonin that binds to mannose, N-acetylglucosamine (NAG)-containing carbohydrates, and various other carbohydrates that are present on the surface of many microbial pathogens. MBL (also called mannose- or mannan-binding protein, MBP) is a polymeric protein assembled from three or more 32 kDa monomers. Each monomer has an N-terminal cysteine rich region, a collagen-like gly-X-Y region, a neck region and a carbohydrate recognition domain. The assembly of the higher molecular weight (MW) polymers begins with formation of trimers of the 32 kDa monomer; these trimers then self-assembly into higher MW polymers of three to six sets of trimers. See FIG. 1.

MBL is a key component in opsonization of microbial pathogens and in the activation of complement (via the lectin pathway) and coagulation. Opsonization is the binding of proteins to target cells and the targeting these cells for uptake and destruction by phagocytic cells, such as macrophages and neutrophils. This opsonization appears to be mediated by the small, cysteine-rich N-terminal domain of MBL as well as C3b deposited on the target cell surface by MBL-mediated lectin complement pathway activation.

In the activation of complement via the lectin pathway, the microbe and specialized proteins, i.e., MASP-1 (Mannan-binding lectin Associated Serine Protease) (Matsushita & Fujita, 176 J. Exp. Med. 1497 (1992)), and MASP-2 (Thiel et al., 386 Nat. 506 (1997)), interact with bound MBL and activate complement in the absence of antibody. The higher molecular weight MBL complexes (5 to 6 repeats of the functional MBL trimer) are potent activators of complement via this lectin pathway, in which MASP 2 appears to activate complement, and MASP 1 activates coagulation. The smaller complexes (three to four repeats of the MBL trimer unit) are the most potent activators of coagulation. Krarup et al., 2 PLoS One e623 (2007).

In certain human populations, there is a high allele frequency of mutations in MBL in the collagen helix, at codons 52, 54, and 57. Garred et al., 7 Genes Immun. 85 (2006). These mutations prevent the formation of the higher molecular weight MBL forms and suppress complement activation. In these cases, MBL still functions as an opsonin and stimulates coagulation, but without activating complement. There is also some evidence for heterozygote advantage with respect to sepsis, in that heterozygotes have the best survival, homozygous "wild-type" second best, and homozygous "mutant" have the worst survival. See Sprong et al., 49 Clin. Infect Dis. 1380 (2009). In addition, homozygous mutant neonates are particularly susceptible to infection before the acquired immune system begins to function.

There has been much debate on the usefulness of MBL as a recombinant therapeutic protein for treatment of infectious diseases. Intact MBL has been used in Phase 1 and Phase 2 clinical trials, both as a recombinant protein and when purified from human blood donations. In fact, plasma-derived MBL has been used as a therapeutic in Phase 1 and Phase II trials of MBL deficient, pediatric patients with chemotherapy induced neutropenia. Frakking et al., 45 Eur. J. Cancer 50 (2009). Commercial efforts to develop MBL have foundered because of difficulties in both producing the recombinant protein and establishing efficacy. As used herein, treatment or treating a subject can refer to medical care provided to manage, improve, or relieve disease, illness, or symptoms thereof.

Figure 5:
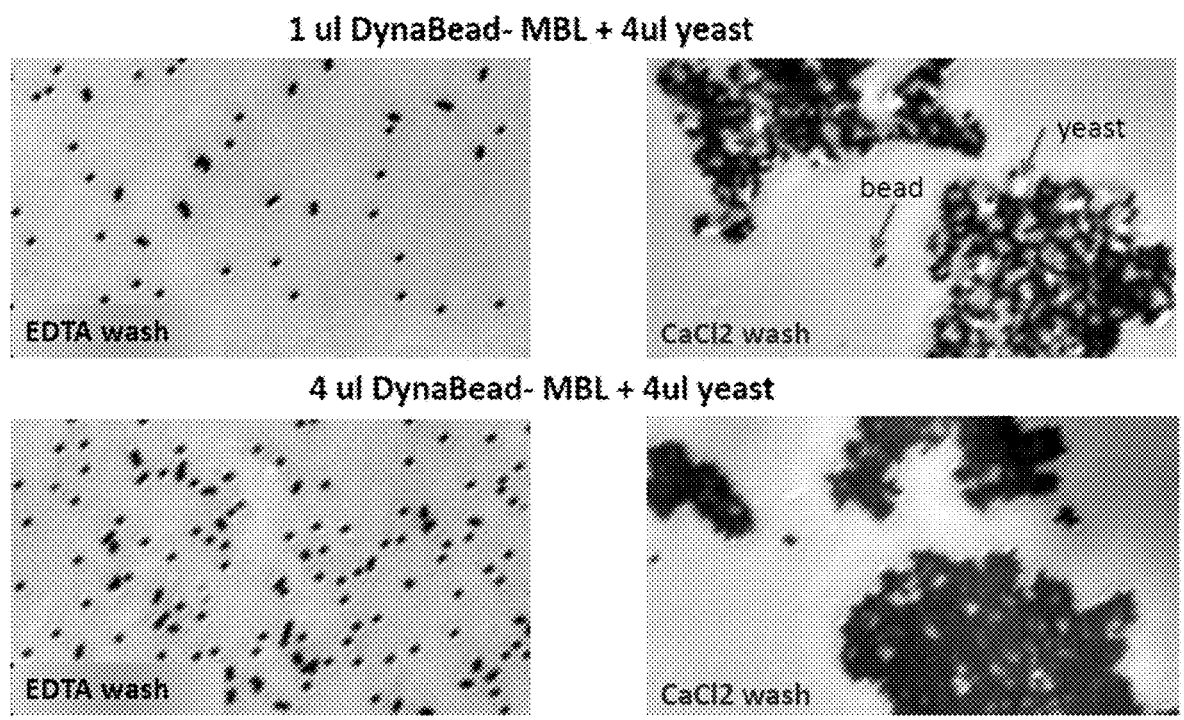
FIG. 5 shows the calcium-dependent binding of dynabead-MBL to C. albicans in which calcium maintains binding and EDTA destabilizes binding.
Figure 6:
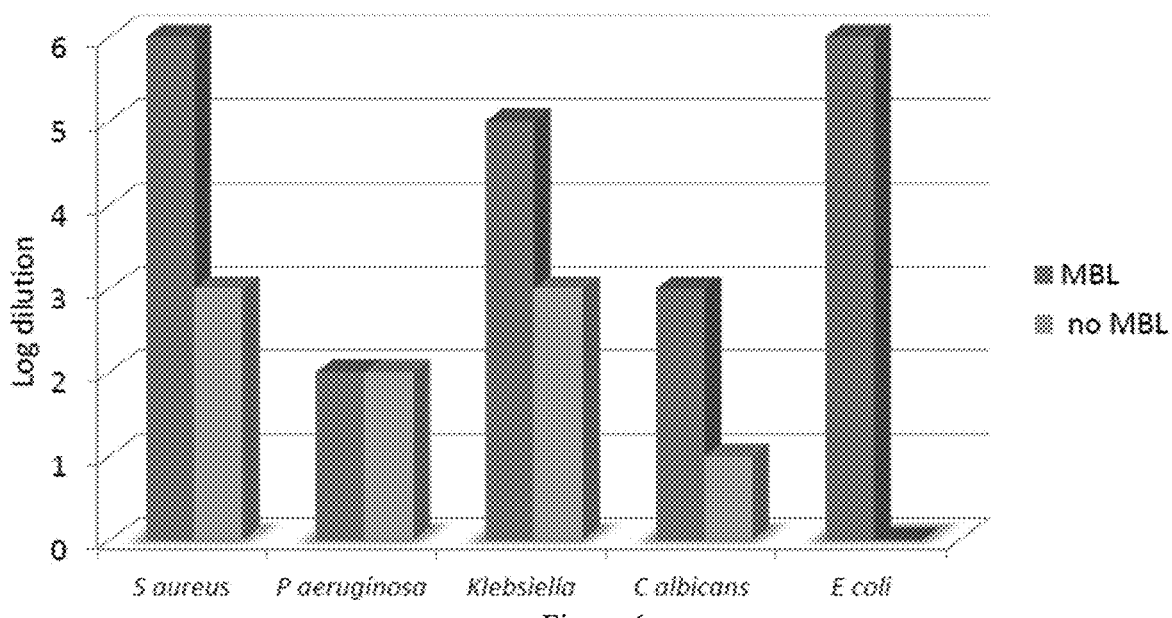
FIG. 6 shows the binding of MBL-magnetic beads to different pathogens. Pathogens were bound by MBL-coated magnetic beads (control: beads without MBL), washed, and eluted onto culture plates.
Figure 7:
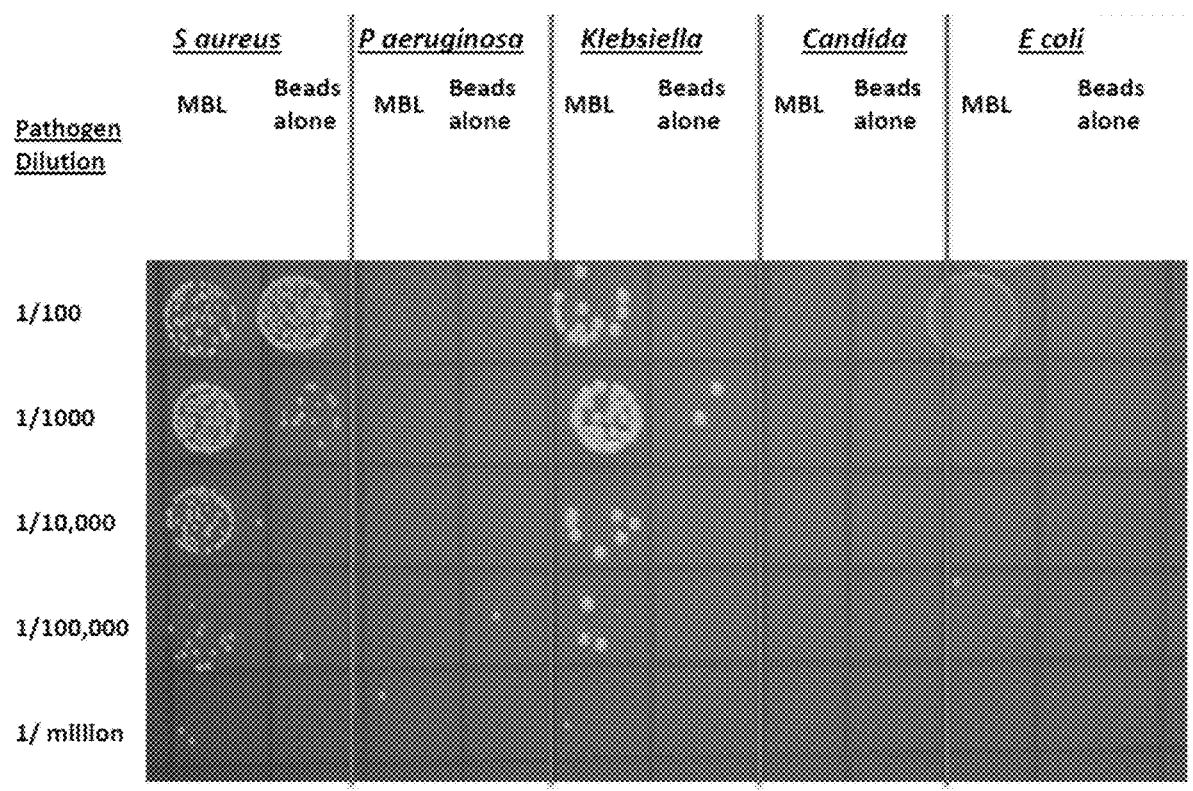
FIG. 7 shows data from MBL-magnetic beads binding to microorganisms and overnight culture assay. The pathogens were bound by MBL-coated magnetic beads (control: beads without MBL), washed, and eluted onto culture plates and incubated overnight.

The present invention provides for engineered opsonins, e.g., engineered MBL or MBL polymers, for use in devices and systems for pathogen detection and clearance. FIG. 5 shows the calcium-dependent binding of MBL-conjugated magnetic microbeads to the yeast *C. albicans*. FIGS. 6 and 7 compare the MBL-magnetic bead binding between several difference pathogens, including the gram positive bacterium, *S. aureus*; gram negative bacteria, *Klebsiella* and *E. coli*; and yeast, *C. albicans*. Recent work has demonstrated the feasibility of using combined micromagnetic and microfluidic techniques to clear living pathogens from flowing fluids, such as biological fluids, such as blood. Xia et al., 8 Biomed. Dev. Biomed. Microdev. 299 (2006); Yung et al., Lab on a Chip DOI: 10.1039/b816986a (2009). In these microdevices (magnetic microbeads that are coated with molecules that bind specifically to surface markers on pathogen cells), are allowed to bind to these cells in whole human blood, and then are pulled free from blood flowing through microfluidic channels using an applied magnetic field gradient. See WO/2008/130618; WO/2007/044642.

Among other uses, these devices have great promise to rapidly clear blood of septic patients of toxin-producing pathogens, and hence greatly increase response to conventional antibiotic therapies. The ability to rapidly (within minutes) bind, detect and isolate living pathogens circulating in blood, or present within other biological fluids, using a potentially inexpensive and easy-to-use microdevice also circumvents the major limitations of current pathogen detection and sensitivity testing assays that require multiple days of microbial culture in hospital or commercial laboratories.

Biological fluids that may by used in the present invention include, for example, blood, cerebrospinal fluid, joint fluid, urine, semen, saliva, tears, and fluids collected by insertion of a needle. Additionally, fluids may be collected from food or water samples for rapid, general contamination assays according to the present invention: such fluid can be collected and analyzed for natural microbial contamination or for possible "bio-terrorism" contamination.

Further, the current effectiveness of these methods harnesses prior knowledge of the specific pathogen that one desires to clear from the blood, because a specific ligand for that pathogen (e.g., specific antibody) is placed on the magnetic microbeads prior to using the blood cleansing device. Thus, the present invention bolsters the current approaches by providing engineered generic binding molecules that function like biological opsonins and bind to specific, many or all, types of microbial pathogens as the application requires. In this regard, the present invention has therapeutic applications.

Another need addressed herein is the development of specialized pathogen class-specific opsonins that bind, for example, all types of fungi or all gram negative bacteria or all or specific gram positive bacteria or all viruses or all protozoans, as this knowledge could quickly advise physicians in their choice of anti-microbial therapies before complete characterization of species type of antibiotic sensitivity is identified with conventional methods that often take many days to complete.

In addition, with the use of genetic engineering, and directed evolution and selection strategies, modified versions of natural opsonins can be engineered, such as MBL, that bind to pathogens in a species-specific manner. Finally, binding that is specific for pathogen sensitivity to different antibiotics or antimicrobial therapeutics can be accomplished using appropriate selection strategies. Hence, this invention provides for development of engineered opsonins that provide these high value properties.

MBL is an excellent choice for use as a generic opsonin for the purposes described herein; however, the intact molecule is not typically used in the presence of whole blood because it has multiple functional domains that promote blood coagulation that may interfere with diagnostic and therapeutic microdevice function. This characteristic of MBL can be separated from its pathogen binding function as provided herein. More specifically, MBL contains four parts, from N- to C-terminus: a small N-terminal domain of essentially unknown function that may be involved in macrophage binding and/or MASP binding; a collagen segment that may also be involved in MASP binding and higher-order oligomerization; an alpha-helical "neck" segment that is sufficient for trimerization; and the CRD lectin domain at the C-terminus that mediates direct pathogen binding. The lectin domain is useful for the application at hand, and the other domains may be present or deleted depending on the needs of the user, and can be determined by routine testing. Additionally, the lectin activity is calcium-dependent, so bound microbes could be released by a chelating agent for diagnostic purposes.

Figure 2A:
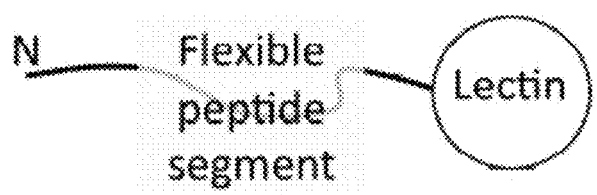
FIGS. 2A and 2B are diagrams of an embodiment of the present invention in which an artificial protein (FIG. 2A) comprising a sterically unhindered N-terminus (optionally with a cysteine at or near the N-terminus), followed by a long, flexible peptide segment, then an MBL lectin domain at the C-terminus, is crosslinked to a solid substrate in the example device in FIG. 2B.
Figure 2B:
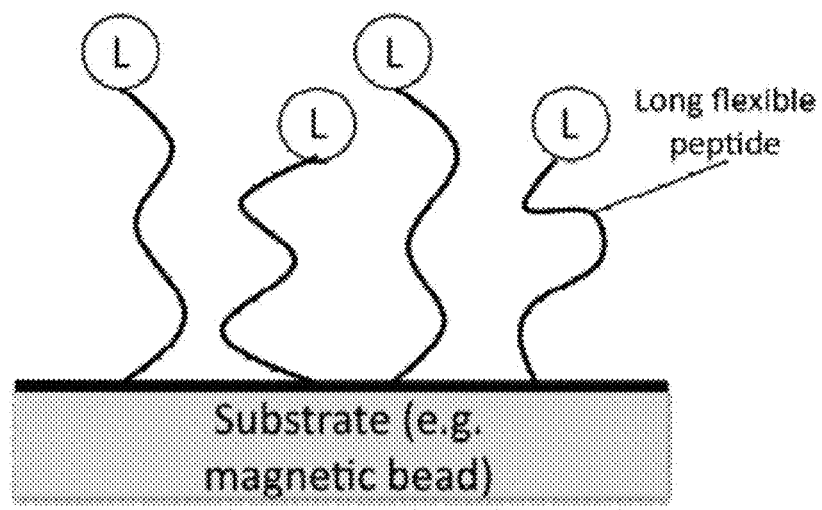

One embodiment of an engineered configuration of MBL, useful as a generic opsonin for diagnostic and therapeutic applications, comprises the lectin domain of MBL. For example, Glycine 111 (as defined in the Research Collaboratory for Structural Bioinformatics (RCSB), Protein Data Bank structure file 1HUP) is a convenient N-terminal point at which to begin the lectin portion of the engineered opsonin. Because the binding of MBL to a given monomeric sugar is weak, the MBL may be attached to the solid matrix in a flexible manner so that the proteins on the surface can move and adjust to the shape of the microbe. For example, a flexible peptide, such as one or more Glycine+Serine segment or one or more Proline+Alanine+Serine segment, or other peptide linker(s) known in the art, may be placed at the MBL N-terminus, as in FIG. 2A, because these segments tend to not form folded structures.

Another embodiment of an engineered configuration of MBL, useful as a generic opsonin for diagnosis and therapeutic applications, comprises the neck and lectin domains of MBL. Proline 81 (as defined, for example, in the Research Collaboratory for Structural Bioinformatics, Protein Data Bank (RCSB PDB) structural file 1HUP) is a convenient N-terminal point at which to begin the lectin sequence for this engineered opsonin construct. This portion of MBL is fused downstream (C-terminal) to Fc portion of human IgG (Fcγ). The Fc portion may include the CH2-CH3 interface of the IgG Fc domain, which contains the binding sites for a number of Fc receptors including Staphylococcal protein A. In use, the Fc portion dimerizes and strengthens the avidity affinity of the binding by MBL lectins to monomeric sugars. Additionally, when used as a diagnostic reagent, the n-linked glycosylation of the recombinant opsonin can be removed. For example, in Fc MBL.81 the glycosylation can be removed by changing the amino acid at residue 297 from asparagine to aspartic acid (N297D) in the Kabat system of numbering amino acids in antibodies, this corresponds to amino acid 82 in this particular Fc construct. Glycosylated Fc maintains the correct orientation for Fc mediated antibody-dependent cell-mediated cytotoxicity (ADCC) and complement-mediated cytotoxicity (CDC).

The engineered Fc MBL opsonin could be used in the activation of Fc receptor-mediated uptake of Fc MBL opsonized *Mycobacterium tuberculosis*, bypassing mannose receptor mediated uptake of *M. tuberculosis*. Recent publications (Kang et al., 202 J. Exp. Med. 987 (2005)), suggest that lipoarabinomannan (ManLaM) on the cells surface of *M. tuberculosis* engage macrophage mannose receptor (MMR) during the phagocytic process. This directs *M. tuberculosis* to its initial phagosomal niche and inhibits phagosome-lysosome (P-L) fusion, thereby enhancing survival in human macrophages. Interestingly, inhibition of P-L fusion did not occur with entry via Fcγ receptors. In one embodiment, uptake by Fc recetor endocytosis routes the bacterium, e.g., *M. tuberculosis*, to different intracellular vesicles.

The configuration of the engineered opsonin of the present invention also aids attachment of the fusion protein to a substrate, such as a solid surface of a magnetic microbead or a microporous membrane, using a chemical cross-linker that is specific for the amino group at the N-terminus, or to a free cysteine residue that has been engineered to be near the N-terminus of the protein, as in FIG. 2B. (Lysine is an alternative to cysteine, optionally following removal of the rest of the lysine residues in the protein).

In some embodiments, the substrate to which the opsonin binds is a living cell or extracellular matrix of a tissue or organ. For example, the substrate may be the surface of a cell, tissue or organ associated with the immune response. For example, the cell may be a phagocyte (macrophage, neutrophil, and dendritic cell), mast cell, eosinophil, basophil, and/or natural killer cell. The cell may be the cell of tissues or organs of the immune system, such as spleen, lymph nodes, lymphatic vessels, tonsils, thymus, bone marrow, Peyer's patches, connective tissues, mucous membranes, the reticuloendothelial system, etc. The surface to which the opsonin binds may also be the extracellular matrix of one or more of these tissues or organs.

In some embodiments, the solid substrate may comprise magnetic beads or other structured materials, which then pull microbes out from fluids, including biological fluids such as blood, and concentrate and collect the microbes, including living microbes. This approach is advantageous because the beads can then be examined for the presence of the microbe, or be used to transfer the collected microbes to conventional pathogen culture and sensitivity testing assays. In other words, the engineered opsonin may be used in diagnostics as a means of collecting potential pathogens for identification; not only in the diagnosis of disease, but in the identification of water- or food-borne pathogens, particulates or other contaminants. Alternatively, the solid substrate may comprise a hollow-fiber reactor or any other blood filtration membrane or flow device (e.g., a simple dialysis tube) or other resins, fibers, or sheets to selective bind and sequester the biological pathogens.

The magnetic beads can be of any shape, including but not limited to spherical, rod, elliptical, cylindrical, disc, and the like. In some embodiments, magnetic beads having a true spherical shape and defined surface chemistry are used to minimize chemical agglutination and non-specific binding. As used herein, the term "magnetic beads" refers to a nano- or micro-scale particle that is attracted or repelled by a magnetic field gradient or has a non-zero magnetic susceptibility. The magnetic bead can be paramagnetic or super-paramagnetic. In some embodiments, magnetic beads are super-paramagnetic. Magnetic beads are also referred to as magnetic particles herein. In some embodiments, magnetic beads having a polymer shell are used to protect the pathogen from exposure to iron. For example, polymer-coated magnetic beads can be used to protect pathogens from exposure to iron.

The magnetic beads can range in size from 1 nm to 1 mm. For example, magnetic beads are about 250 nm to about 250 μm in size. In some embodiments, magnetic bead is 0.1 μm to 100 μm in size. In some embodiments, magnetic bead is 0.1 μm to 50 μm in size. In some embodiments, magnetic bead is 0.1 μm to 10 μm in size. In some embodiments, the magnetic bead is a magnetic nano-particle or magnetic micro-particle. Magnetic nanoparticles are a class of nanoparticle which can be manipulated using magnetic field or magnetic field gradient. Such particles commonly consist of magnetic elements such as iron, nickel and cobalt and their chemical compounds. Magnetic nano-particles are well-known and methods for their preparation have been described in the art. See, e.g., U.S. Pat. Nos. 6,878,445; 5,543,158; 5,578,325; 6,676,729; 6,045,925; and 7,462,446; and U.S. Patent Publications No. 2005/0025971; No. 2005/0200438; No. 2005/0201941; No. 2005/0271745; No. 2006/0228551; No. 2006/0233712; No. 2007/01666232; and No. 2007/0264199.

Magnetic beads are easily and widely available commercially, with or without functional groups capable of binding to affinity molecules. Suitable magnetic beads are commercially available such as from Dynal Inc. (Lake Success, N.Y.); PerSeptive Diagnostics, Inc. (Cambridge, Mass.); Invitrogen Corp. (Carlsbad, Calif.); Cortex Biochem Inc. (San Leandro, Calif.); and Bangs Laboratories (Fishers, Ind.). In particular embodiments, magnetic particles are MyOne™ Dynabeads® magnetic beads (Dynal Inc.).

The solid substrate can be fabricated from or coated with a biocompatible material. As used herein, the term "biocompatible material" refers to any material that does not deteriorate appreciably and does not induce a significant immune response or deleterious tissue reaction, e.g., toxic reaction or significant irritation, over time when implanted into or placed adjacent to the biological tissue of a subject, or induce blood clotting or coagulation when it comes in contact with blood. Suitable biocompatible materials include, for example, derivatives and copolymers of a polyimides, poly(ethylene glycol), polyvinyl alcohol, polyethyleneimine, and polyvinylamine, polyacrylates, polyamides, polyesters, polycarbonates, and polystyrenes.

In some embodiments, the solid substrate is fabricated or coated with a material selected from the group consisting of polydimethylsiloxane, polyimide, polyethylene terephthalate, polymethylmethacrylate, polyurethane, polyvinylchloride, polystyrene polysulfone, polycarbonate, polymethylpentene, polypropylene, a polyvinylidine fluoride, polysilicon, polytetrafluoroethylene, polysulfone, acrylonitrile butadiene styrene, polyacrylonitrile, polybutadiene, poly(butylene terephthalate), poly(ether sulfone), poly(ether ether ketones), poly(ethylene glycol), styrene-acrylonitrile resin, poly(trimethylene terephthalate), polyvinyl butyral, polyvinylidenedifluoride, poly(vinyl pyrrolidone), and any combination thereof.

In an aspect of the invention, the recombinant opsonins described herein can be conjugated with the solid substrate by methods well known in the art for conjugating peptides with other molecules. For example, Hermanson, BIOCONJUGATE TECHNIQUES (2nd Ed., Academic Press (2008)) and Niemeyr, *Bioconjugation Protocols: Strategies & Methods*, in METHODS IN MOLECULAR BIOLOGY (Humana Press, 2004), provide a number of methods and techniques for conjugating peptides to other molecules. de Graaf, et al., 20 Biocojugate Chem. 1281 (2009), provides a review of site-specific introduction of non-natural amino acids into peptides for conjugation.

Alternatively, the surface of the solid substrate can be functionalized to include binding molecules that bind selectively with the recombinant opsonin. These binding molecules are also referred to as affinity molecules herein. The binding molecule can be bound covalently or non-covalently on the surface of the solid substrate. As used herein, the term "binding molecule" or "affinity molecule" refers to any molecule that is capable of specifically binding a recombinant opsonin described herein. Representative examples of affinity molecules include, but are not limited to, antibodies, antigens, lectins, proteins, peptides, nucleic acids (DNA, RNA, PNA and nucleic acids that are mixtures thereof or that include nucleotide derivatives or analogs); receptor molecules, such as the insulin receptor; ligands for receptors (e.g., insulin for the insulin receptor); and biological, chemical or other molecules that have affinity for another molecule, such as biotin and avidin. The binding molecules need not comprise an entire naturally occurring molecule but may consist of only a portion, fragment or subunit of a naturally or non-naturally occurring molecule, as for example the Fab fragment of an antibody. The binding molecule may further comprise a marker that can be detected.

The binding molecule can be conjugated to surface of the solid substrate using any of a variety of methods known to those of skill in the art. The binding molecule can be coupled or conjugated to surface of the solid substrate covalently or non-covalently. Covalent immobilization may be accomplished through, for example, silane coupling. See, e.g., Weetall, 15 Adv. Mol. Cell Bio. 161 (2008); Weetall, 44 Meths. Enzymol. 134 (1976). The covalent linkage between the binding molecule and the surface can also be mediated by a linker. The non-covalent linkage between the affinity molecule and the surface can be based on ionic interactions, van der Waals interactions, dipole-dipole interactions, hydrogen bonds, electrostatic interactions, and/or shape recognition interactions.

As used herein, the term "linker" means a molecular moiety that connects two parts of a composition. Peptide linkers may affect folding of a given fusion protein, and may also react/bind with other proteins, and these properties can be screened for by known techniques. Example linkers, in addition to those described herein, include is a string of histidine residues, e.g., His6; sequences made up of Ala and Pro, varying the number of Ala-Pro pairs to modulate the flexibility of the linker; and sequences made up of charged amino acid residues e.g., mixing Glu and Lys. Flexibility can be controlled by the types and numbers of residues in the linker. See, e.g., Perham, 30 Biochem. 8501 (1991); Wriggers et al., 80 Biopolymers 736 (2005). Chemical linkers may comprise a direct bond or an atom such as oxygen or sulfur, a unit such as NH, C(O), C(O)NH, SO, $SO_2$, $SO_2$NH, or a chain of atoms, such as substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_6$-$C_{12}$ aryl, substituted or unsubstituted $C_5$-$C_{12}$ heteroaryl, substituted or unsubstituted $C_5$-$C_{12}$ heterocyclyl, substituted or unsubstituted $C_3$-$C_{12}$ cycloalkyl, where one or more methylenes can be interrupted or terminated by O, S, S(O), $SO_2$, NH, or C(O).

Nucleic acid based binding molecules include aptamers. As used herein, the term "aptamer" means a single-stranded, partially single-stranded, partially double-stranded or double-stranded nucleotide sequence capable of specifically recognizing a selected non-oligonucleotide molecule or group of molecules by a mechanism other than Watson-Crick base pairing or triplex formation. Aptamers can include, without limitation, defined sequence segments and sequences comprising nucleotides, ribonucleotides, deoxyribonucleotides, nucleotide analogs, modified nucleotides and nucleotides comprising backbone modifications, branchpoints and nonnucleotide residues, groups or bridges. Methods for selecting aptamers for binding to a molecule are widely known in the art and easily accessible to one of ordinary skill in the art.

The recombinant opsonin can be conjugated with surface of the solid substrate by an affinity binding pair. The term "affinity binding pair" or "binding pair" refers to first and second molecules that specifically bind to each other. One member of the binding pair is conjugated with the solid substrate while the second member is conjugated with the recombinant opsonin. As used herein, the term "specific binding" refers to binding of the first member of the binding pair to the second member of the binding pair with greater affinity and specificity than to other molecules.

Exemplary binding pairs include any haptenic or antigenic compound in combination with a corresponding antibody or binding portion or fragment thereof (e.g., digoxigenin and anti-digoxigenin; mouse immunoglobulin and goat antimouse immunoglobulin) and nonimmunological binding pairs (e.g., biotin-avidin, biotin-streptavidin), hormone (e.g., thyroxine and cortisol-hormone binding protein), receptor-receptor agonist, receptor-receptor antagonist (e.g., acetylcholine receptor-acetylcholine or an analog thereof), IgG-protein A, lectin-carbohydrate, enzyme-enzyme cofactor, enzyme-enzyme inhibitor, and complementary oligonucleoitde pairs capable of forming nucleic acid duplexes), and the like. The binding pair can also include a first molecule that is negatively charged and a second molecule that is positively charged.

One example of using binding pair conjugation is the biotin-sandwich method. See, e.g., Davis et al., 103 PNAS 8155 (2006). The two molecules to be conjugated together are biotinylated and then conjugated together using tetravalent streptavidin as a linker. A peptide can be coupled to the 15-amino acid sequence of an acceptor peptide for biotinylation (referred to as AP; Chen et al., 2 Nat. Methods 99 (2005)). The acceptor peptide sequence allows site-specific biotinylation by the E. coli enzyme biotin ligase (BirA; Id.). A recombinant opsonin can be similarly biotinylated for conjugation with a solid substrate. Many commercial kits are also available for biotinylating proteins. Another example for conjugation to a solid surface would be to use PLP-mediated bioconjugation. See, e.g., Witus et al., 132 JACS 16812 (2010). In this example, an AKT sequence on the Fc N terminal allows conjugation to the solid surface and orientation of the lectin binding domain in the optimal orientation pointing away from the solid surface.

It should be noted that the affinity of a single lectin domain for a sugar is low, and binding is normally driven by avidity and multivalency. In the case of the present devices, the multimerization domains are deleted from the protein, and multivalency of the protein is effectively produced by attachment to a solid substrate (e.g., a bead) at high density, which density can be varied to provide optimal functionality.

Further regarding the MBL, its binding characteristics can be manipulated by directed evolution for altered binding specificity. MBL may be modified so that it binds to a more limited set of sugars or other molecular features, with the result that the modified MBL will bind to a more limited set of microbes to provide a capability for pathogen class identification (e.g., one of virus, bacteria, fungi, or protozoan), subclass typing (e.g., gram negative or gram positive bacteria) or specific species determination. Numerous strategies are available in the art.

For example, a straightforward directed evolution strategy visually examines an atomic structure of MBL complexed with a sugar, and then mutates appropriate amino acids that make contact in a sugar-specific manner, so that distinctive contacts are lost or particular types of steric hindrance are created. The three dimensional structure of rat MBL has been solved in a complex with a high-mannose oligosaccharide and with N-acetylglucosamine, a methylated fucose, and so on. His189Val and Ile207Val are examples of substitutions that modifications alter specificity.

In another strategy of directed evolution, the protein is subjected to random mutagenesis and the resulting proteins are screened for desired qualities. This is a particularly useful technology for affinity maturation of phage display antibodies, where the antibody complementary determining regions (CDRs) are mutated by saturation mutagenesis and successful variants of the six CDRs are shuffled together to form the highest affinity antibodies.

The directed evolution paradigm can be applied to MBL in order to select MBL variants with specific binding to yeast, gram-positive bacteria, gram-negative, coagulase negative, aerobic bacteria, etc. For this to work, however, the pattern and nature of the target sugars or related surface features on these target organisms may have to differ between the classes or species.

MBL is known to bind strongly to mannose and N-acetylglucosamine sugars on fungi, gram-positive, and gram-negative bacteria. For example, MBL binds strongly to *Candida* spp., *Aspergillus fumigatus, Staphylococcus aureus*, and β hemolytic group A streptococci. MBL has intermediate affinity to *Escherichia coli, Klebsiella* spp., and *Haemophilus influenzae* type b. MBL binds weakly to β hemolytic group B streptococci, *Streptococcus pneumoniae*, and *Staphylococcus epidermidis*. Neth et al., 68 Infect. & Immun. 688 (2000). The capsular polysaccharide of *Neisseria meningitides* serogroup B, *H. influenzae* type b and *Cryptococcus neoformans* are thought to decrease MBL binding, as does bacterial endotoxin. Id.; Van Emmerik et al., 97 Clin. Exp. Immunol. 411 (1994); Schelenz et al., 63 Infect. Immun. 3360 (1995).

Others have reported that MBL facilitates opsonophagocytosis of yeasts but not of bacteria, despite MBL binding: MBL (Lectin) pathway of complement was critical for the opsonophagocytosis of yeast, but the classical complement pathway was critical for opsonophagocytosis of bacteria. Brouwer et al., 180 J. Immunol. 4124 (2008). It was not reported that MBL bound to the bacterial species tested, however, only that MBL binding did not promote significant complement activation and opsonophagocytosis.

Derivatives of MBL with a particular specificity can be isolated by the following approach, which is a standard phage display strategy: First, express a set of MBL variants from a phagemid vector; then bind this library to a target of interest (e.g., *E. coli*) and perform one or two rounds of selection; and then perform a round of negative selection against a related target (e.g., *Candida*), taking those phagemids that fail to bind. These cycles of positive and negative selection are then repeated until a population of phages that generally bind to the target and do not bind to the non-target is generated. This method may be applied to any pair of microbial strains against which differential binding is desired, such as bacteria that are resistant and sensitive to a given antibiotic. This positive/negative enrichment strategy may also be used with an antibody-phage display library, which is an even more standard way to isolate such specific binders.

MBL belongs to the class of collectins in the C-type (calcium-dependent) lectin superfamily, other members of which, such as surfactant protein A, surfactant protein D, CL-L1 and CL-P1, may be useful in the present invention. Other possible opsonins include ficollins (Thiel et al., 1997), which also activate the lectin pathway of complement and bind MASP proteins. These proteins are related to MBL but have a different, more limited specificity. In the context of the diagnostic device described herein, one option is to simply use the lectin domain of a ficollin that corresponds to the lectin domain of MBL described above. Another approach is to use 'shuffling' of segments or individual amino acids between MBL and one or more Ficollins to create hybrid molecules that may have hybrid specificities. The directed evolution and selection approach described above also could potentially be used to generate human antibody fragments or peptides that provide the class, subclass and species specificity described above.

The present invention may be defined in any of the following numbered paragraphs:

1. A recombinant opsonin comprising: a carbohydrate recognition domain of an opsonin; a substrate binding domain; and a peptide domain that links the recognition domain to the substrate binding domain.

2. The recombinant opsonin of paragraph 1, wherein said carbohydrate recognition domain is a collectin or ficollin or derived from a collectin or ficollin.

3. The recombinant opsonin of paragraph 1, wherein said carbohydrate recognition domain is a lectin or a portion or a fragment of a lectin.

4. The recombinant opsonin of paragraph 3, wherein said lectin is mannose-binding lectin (MBL).

5. The recombinant opsonin of paragraph 4, wherein the lectin consists of amino acid residues 81 (proline) to 228 (isoleucine) of MBL (SEQ ID NO:2).

6. The recombinant opsonin of any of the foregoing paragraphs, wherein said substrate binding domain comprises at least one cysteine residue that allows chemical cross-linking to a solid substrate.

7. The recombinant opsonin of any of the foregoing paragraphs, wherein the flexible peptide comprises a Glycine+Serine segment or a Proline+Alanine+Serine segment.

8. The recombinant opsonin of the foregoing paragraphs, where the flexible peptide comprises a portion of immunoglobulin Fc.

9. The recombinant opsonin of paragraph 8, wherein the Fc portion includes the CH2-CH3 interface of the IgG Fc domain.

10. The recombinant opsonin of any of the foregoing paragraph, wherein the substrate is a magnetic microbead, a paramagnetic microbead, a microporous membrane, a hollow-fiber reactor, or any other fluid filtration membrane or flow device.

11. The recombinant opsonin of any of the foregoing paragraphs, wherein the substrate is a living cell or extracellular matrix of a biological tissue or organ.

12. The recombinant opsonin of paragraph 11, wherein the substrate is a phagocyte.

13. A method of collecting an opsonin-binding microorganism from a fluid comprising contacting the fluid with a recombinant opsonin conjugated to a solid surface; wherein the recombinant opsonin consists of a carbohydrate recognition domain of an opsonin, a solid substrate binding domain, and a flexible peptide domain that links the recognition domain to the solid surface binding domain; allowing the opsonin-binding microorganism to bind to said recombinant opsonin-solid surface conjugate; and separating said fluid from said microorganism-bound recombinant opsonin-solid surface conjugate.

14. The method of paragraph 13, wherein the solid surface is a magnetic particle, and the separating is achieved by applying magnetic force to the fluid after the opsonin-binding microorganism has bound to the recombinant opsonin-solid surface conjugate.

15. The method of paragraph 13, further comprising the step of identifying the microorganism.

16. The method of paragraph 13, wherein the fluid is a biological fluid.

17. The method of paragraph 16, wherein the biological fluid is selected from the group consisting of blood, cerebrospinal fluid, joint fluid, urine, semen, saliva, tears, and fluids collected by needle, biopsy, or aspiration procedures.

18. The method of paragraph 17, wherein the biological fluid is blood.

19. The method of paragraph 18, further comprising the step of returning the blood to its source.

20. The method of paragraph 19, wherein the source is a subject.

21. The method of paragraph 20, wherein the subject is suffering from infection or sepsis.

22. The method of paragraph 13, wherein the fluid is derived from a water or a food sample.

23. The use of the recombinant opsonin of any of paragraphs 1 to 10 in the identification of a pathogen.

24. The use of the recombinant opsonin of any of paragraphs 1 to 10 in the diagnosis of disease.

25. The use of the recombinant opsonin of any of paragraphs 1 to 10 in the identification of water or food contamination.

26. The use of the recombinant opsonin of any of paragraphs 1 to 12 in the treatment of disease.

27. The use of the recombinant opsonin as in paragraph 26, further combined with additional treatment or therapy.

28. A method of treating a blood infection in a subject comprising administering a recombinant opsonin to the blood of the subject, wherein the recombinant opsonin consists of a carbohydrate recognition domain of an opsonin, a substrate binding domain, and a flexible peptide domain that links the recognition domain to the substrate binding domain, wherein the carbohydrate recognition domain binds an opsonin-binding microorganism, and wherein the substrate binding domain binds with a cell, tissue or organ of the immune system; allowing the recombinant opsonin to bind to the opsonin-binding microorganism; and allowing the microorganism-bound recombinant opsonin to bind with a cell, tissue or organ of the immune system wherein the microorganism is killed.

29. The method of paragraph 28, wherein the subject is an animal.

30. The method of paragraph 28, wherein the subject is a human.

EXAMPLES

Example 1. Construction and Expression of FcMBL.81

Figure 3:
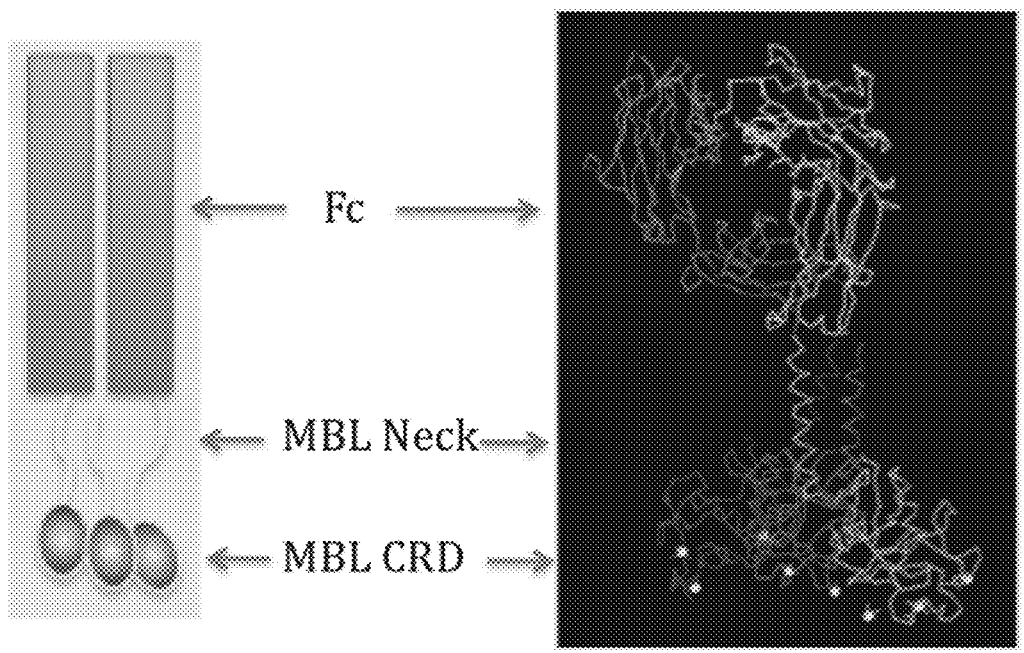
FIG. 3 shows a diagram of an embodiment of the invention, Fc-MBL.81, both in cartoon and in model form based on the X ray crystallography models of Fc and of the neck and carbohydrate recognition domains (CRD) of MBL.
Figure 4:
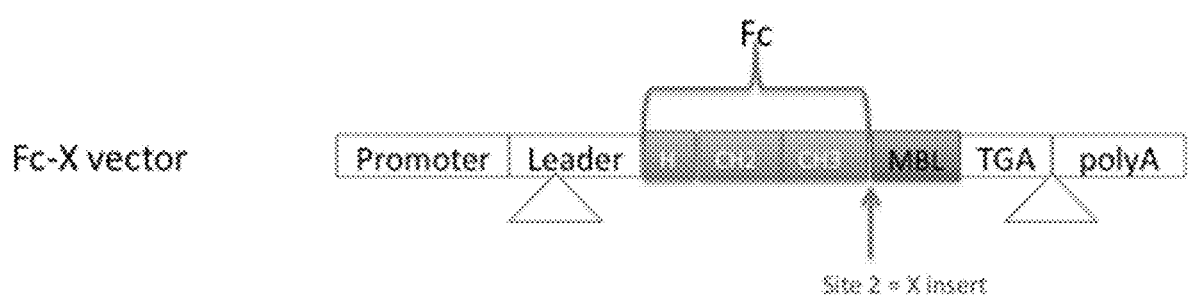
FIG. 4 is a scheme of a vector encoding Fc in an aspect of the invention.

An embodiment of an engineered configuration of MBL, useful as a generic opsonin for diagnosis and therapeutic applications, was constructed using the "neck" and "lectin" domains of MBL. Proline 81 (as defined in the Research Collaboratory for Structural Bioinformatics, Protein Data Bank structural file 1HUP) was selected as the N-terminal point at which to begin the lectin sequence. This portion of the lectin molecule was fused downstream (C-terminal) to Fc portion of human gamma 1 (Fcγ). A diagram of the engineered opsonin construct is shown in FIG. 3. A schematic of the Fc portion of a clone is shown in FIG. 4. The amino acids for this construct include the following residues:

Fc Protein Sequence:

(SEQ ID NO: 1)

```
001 epkssdktht cppcpapell ggpsvflfpp kpkdtlmisr tpevtcvvvd vshedpevkf 061 nwyvdgvevh naktkpreeq ynstyrvvsv ltvlhqdwln gkeykckvsn kalpapiekt 121 iskakgqpre pqvytlppsr deltknqvsl tclvkgfyps diavewesng qpennykttp 181 pvldsdgsff lyskltvdks rwqqgnvfsc svmhealhnh ytqkslslsp ga
```

MBL.81 Protein Sequence (this Includes the Coiled-Coil Neck Region and the Carbohydrate Recognition Domains (CRD) of Human MBL):

(SEQ ID NO: 2)
```
 81 pdgdsslaas erkalqtema rikkwltfsl gkqvgnkffl tngeimtfek vkalcvkfqa 141 svatprnaae ngaiqnlike eaflgitdek tegqfvdltg nrltytnwne gepnnagsde 201 dcvlllkngq wndvpcstsh lavcefpi
```

Fc-MBL.81 Sequence:

(SEQ ID NO: 3)
```
001 epkssdktht cppcpapell ggpsvflfpp kpkdtlmisr tpevtcvvvd vshedpevkf 061 nwyvdgvevh naktkpreeq ynstyrvvsv ltvlhqdwln gkeykckvsn kalpapiekt 121 iskakgqpre pqvytlppsr deltknqvsl tclvkgfyps diavewesng qpennykttp 181 pvldsdgsff lyskltvdks rwqqgnvfsc svmhealhnh ytqkslslsp gapdgdssla 241 aserkalqte marikkwltf slgkqvgnkf fltngeimtf ekvkalcvkf qasvatprna 301 aengaiqnli keeaflgitd ekteggfvdl tgnrltytnw negepnnags dedcvlllkn 361 gqwndvpcst shlavcefpi
```

Thus, the FcMBL.81 construct consists of a lectin having amino acid residues 81 (proline) to 228 (isoleucine) of MBL, fused a portion of Fcγ. In use, the Fc portion dimerizes and adds avidity to the weak affinity of the binding by MBL lectins to monomeric sugars. When Fc MBL.81 is designed for use as a diagnostic reagent, the n-linked glycosylation can be removed by changing the amino acid at 297 from asparagine to aspartic acid (N297D), or amino acid 82 in the Fc construct. Glycosylated Fc is maintains the correct orientation for Fc mediated ADCC and CDC. Additionally, a cysteine residue can be cloned onto the engineered opsonin to allow binding to a solid substrate via chemical conjugation. The construction and expression of an engineered opsonin, such as FcMBL, may be achieved by various techniques known in the art, see, e.g., U.S. Pat. No. 5,541,087.

Figure 8A:
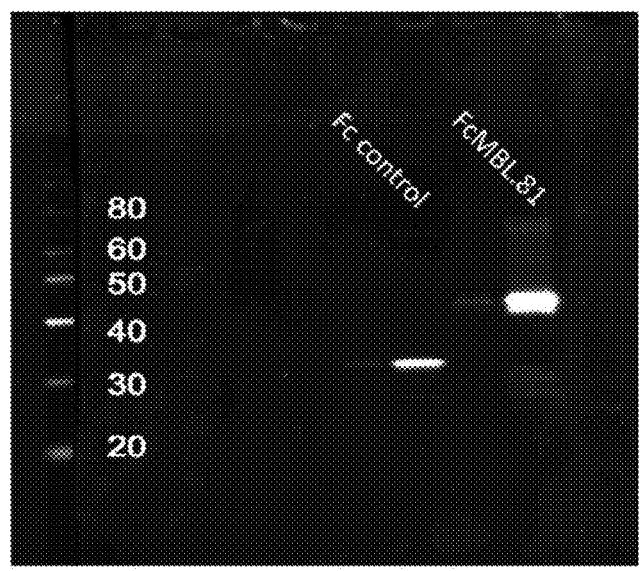
FIGS. 8A and 8B demonstrate high levels of FcMBL expression from transient transfection.
Figure 8B:
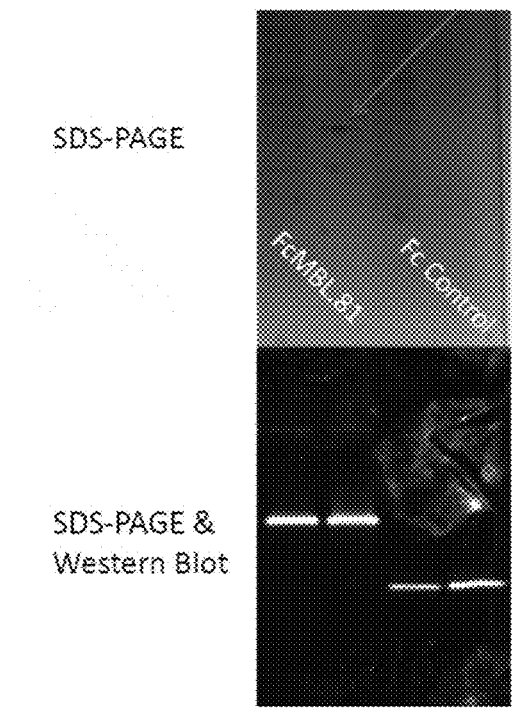

Expression of the construct in transiently transfected cells is demonstrated in FIGS. 8A and 8B. The FcMBL.81 expressed about 35 mg/L.

Figure 9:
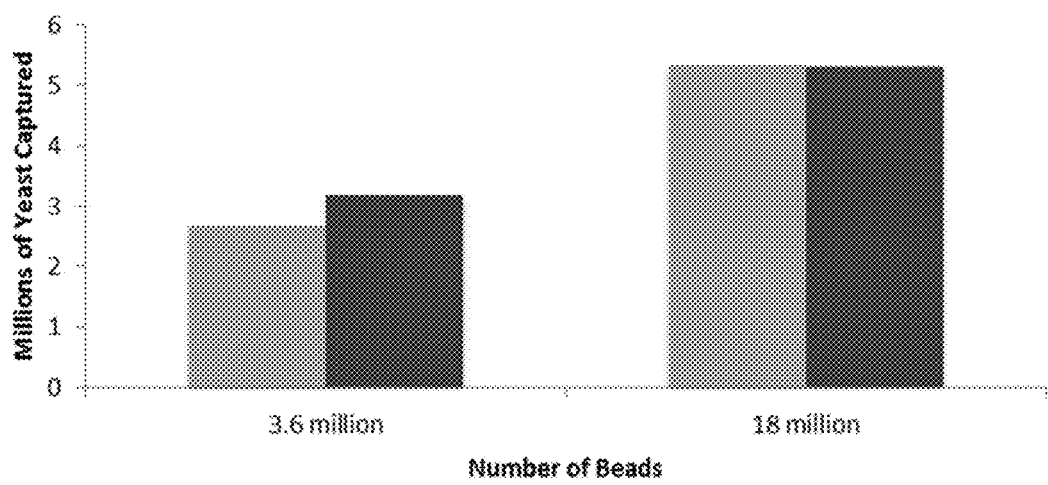
FIG. 9 shows results of a depletion assay in which the FcMBL.81 construct was as active as full-length MBL in binding C. albicans.

Example 2. Comparison of Fc MBL.81 Construct with Full-Length MBL in Binding Yeast Approximately 5.5 million *Candida albicans* yeast cells were inoculated with varying numbers of MBL beads coated with either wild-type, full-length MBL (hexamers of trimers) or Fc MBL.81. As depicted graphically in FIG. 9, 18 million wild-type, full-length MBL or Fc MBL.81 beads bound all 5.5 million fungal cells. This example demonstrates that Fc MBL.81 beads are as active as wild-type, full-length MBL beads in binding to *C albicans*.

We claim:

1. A recombinant opsonin comprising an immunoglobulin Fc fused to a carbohydrate recognition domain (CRD) of a mannose-binding lectin (MBL), wherein the CRD comprises amino acid residues 31 to 148 of SEQ ID NO: 2, and wherein the recombinant opsonin does not comprise the cysteine rich N-terminal domain of the MBL and does not comprise the collagen-like segment of the MBL, wherein the recombinant opsonin is covalently attached to a solid substrate.

2. The recombinant opsonin of claim 1, wherein the solid substrate is selected from the group consisting of a magnetic microbead and a paramagnetic microbead.

3. The recombinant opsonin of claim 1, wherein the amino acid residues 31 to 148 of SEQ ID NO: 2 are C-terminal of the immunoglobulin Fc.

4. The recombinant opsonin of claim 1, wherein the immunoglobulin Fc comprises SEQ ID NO: 1.

5. The recombinant opsonin of claim 1, wherein the solid substrate is selected from the group consisting of: a microporous membrane, a hollow fiber, and a fluid filtration membrane.

* * * * *

SEQUENCE LISTING

```
<160> NUMBER OF SEQ ID NOS: 3

<210> SEQ ID NO 1
<211> LENGTH: 232
<212> TYPE: PRT
<213> ORGANISM: Homo sapiens

<400> SEQUENCE: 1

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80
```

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Ala
225                 230

<210> SEQ ID NO 2
<211> LENGTH: 148
<212> TYPE: PRT
<213> ORGANISM: Homo sapiens

<400> SEQUENCE: 2

Pro Asp Gly Asp Ser Ser Leu Ala Ala Ser Glu Arg Lys Ala Leu Gln
1               5                   10                  15

Thr Glu Met Ala Arg Ile Lys Lys Trp Leu Thr Phe Ser Leu Gly Lys
            20                  25                  30

Gln Val Gly Asn Lys Phe Phe Leu Thr Asn Gly Glu Ile Met Thr Phe
        35                  40                  45

Glu Lys Val Lys Ala Leu Cys Val Lys Phe Gln Ala Ser Val Ala Thr
    50                  55                  60

Pro Arg Asn Ala Ala Glu Asn Gly Ala Ile Gln Asn Leu Ile Lys Glu
65                  70                  75                  80

Glu Ala Phe Leu Gly Ile Thr Asp Glu Lys Thr Glu Gly Gln Phe Val
                85                  90                  95

Asp Leu Thr Gly Asn Arg Leu Thr Tyr Thr Asn Trp Asn Glu Gly Glu
            100                 105                 110

Pro Asn Asn Ala Gly Ser Asp Glu Asp Cys Val Leu Leu Leu Lys Asn
        115                 120                 125

Gly Gln Trp Asn Asp Val Pro Cys Ser Thr Ser His Leu Ala Val Cys
    130                 135                 140

Glu Phe Pro Ile
145

<210> SEQ ID NO 3
<211> LENGTH: 380
<212> TYPE: PRT
<213> ORGANISM: Artificial
<220> FEATURE:
<223> OTHER INFORMATION: Construct Fc-MBL.81

```
<400> SEQUENCE: 3

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Ala Pro Asp Gly Asp Ser Ser Leu Ala
225                 230                 235                 240

Ala Ser Glu Arg Lys Ala Leu Gln Thr Glu Met Ala Arg Ile Lys Lys
                245                 250                 255

Trp Leu Thr Phe Ser Leu Gly Lys Gln Val Gly Asn Lys Phe Phe Leu
            260                 265                 270

Thr Asn Gly Glu Ile Met Thr Phe Glu Lys Val Lys Ala Leu Cys Val
        275                 280                 285

Lys Phe Gln Ala Ser Val Ala Thr Pro Arg Asn Ala Ala Glu Asn Gly
    290                 295                 300

Ala Ile Gln Asn Leu Ile Lys Glu Glu Ala Phe Leu Gly Ile Thr Asp
305                 310                 315                 320

Glu Lys Thr Glu Gly Gln Phe Val Asp Leu Thr Gly Asn Arg Leu Thr
                325                 330                 335

Tyr Thr Asn Trp Asn Glu Gly Glu Pro Asn Asn Ala Gly Ser Asp Glu
            340                 345                 350

Asp Cys Val Leu Leu Leu Lys Asn Gly Gln Trp Asn Asp Val Pro Cys
        355                 360                 365

Ser Thr Ser His Leu Ala Val Cys Glu Phe Pro Ile
    370                 375                 380
```